United States Patent
Kapit

(12) 
(10) Patent No.: US 6,783,359 B2
(45) Date of Patent: Aug. 31, 2004

(54) ORTHODONTIC MARGINAL RIDGE MEASUREMENT DEVICE

(76) Inventor: Arthur L. Kapit, 18064 Sentinel Cir., Boca Raton, FL (US) 33496

( * ) Notice: Subject to any disclaimer, the term of this patent is extended or adjusted under 35 U.S.C. 154(b) by 204 days.

(21) Appl. No.: 10/187,819

(22) Filed: Jul. 3, 2002

(65) Prior Publication Data

US 2004/0005523 A1 Jan. 8, 2004

(51) Int. Cl.[7] .................................................. A61C 3/00
(52) U.S. Cl. ............................. 433/3; 433/72; 433/141
(58) Field of Search .......................... 433/3, 4, 72, 75, 433/141; 33/513, 514

(56) References Cited

U.S. PATENT DOCUMENTS 3,292,118 A * 12/1966 Pastene ........................ 335/37
3,871,098 A * 3/1975 Dean .............................. 433/3
6,296,482 B1 10/2001 Kapit ............................. 433/3

* cited by examiner

Primary Examiner—John J Wilson
(74) Attorney, Agent, or Firm—Gregory J. Gore

(57) ABSTRACT

A marginal ridge attachment plate slides onto the center tab of a height gauge to provide more accurate orthodontic bracket placement. In use, vertically-extending legs on the attachment plate rest on mesial and distal marginal ridges of the tooth. The plate is shaped so that while the legs rest directly on the marginal ridges, a cut-out portion between the legs avoids contact and interference from the inward-facing slopes of the tooth cusps. Therefore, correct bracket height is measured with reference to the marginal ridges of the tooth rather than the tooth cusp.

13 Claims, 2 Drawing Sheets

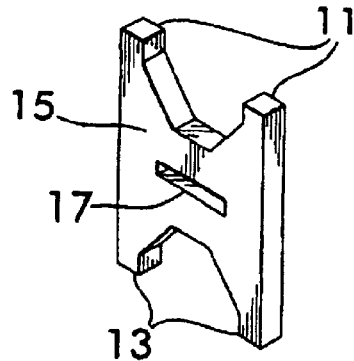
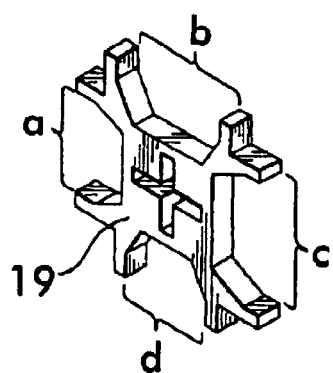
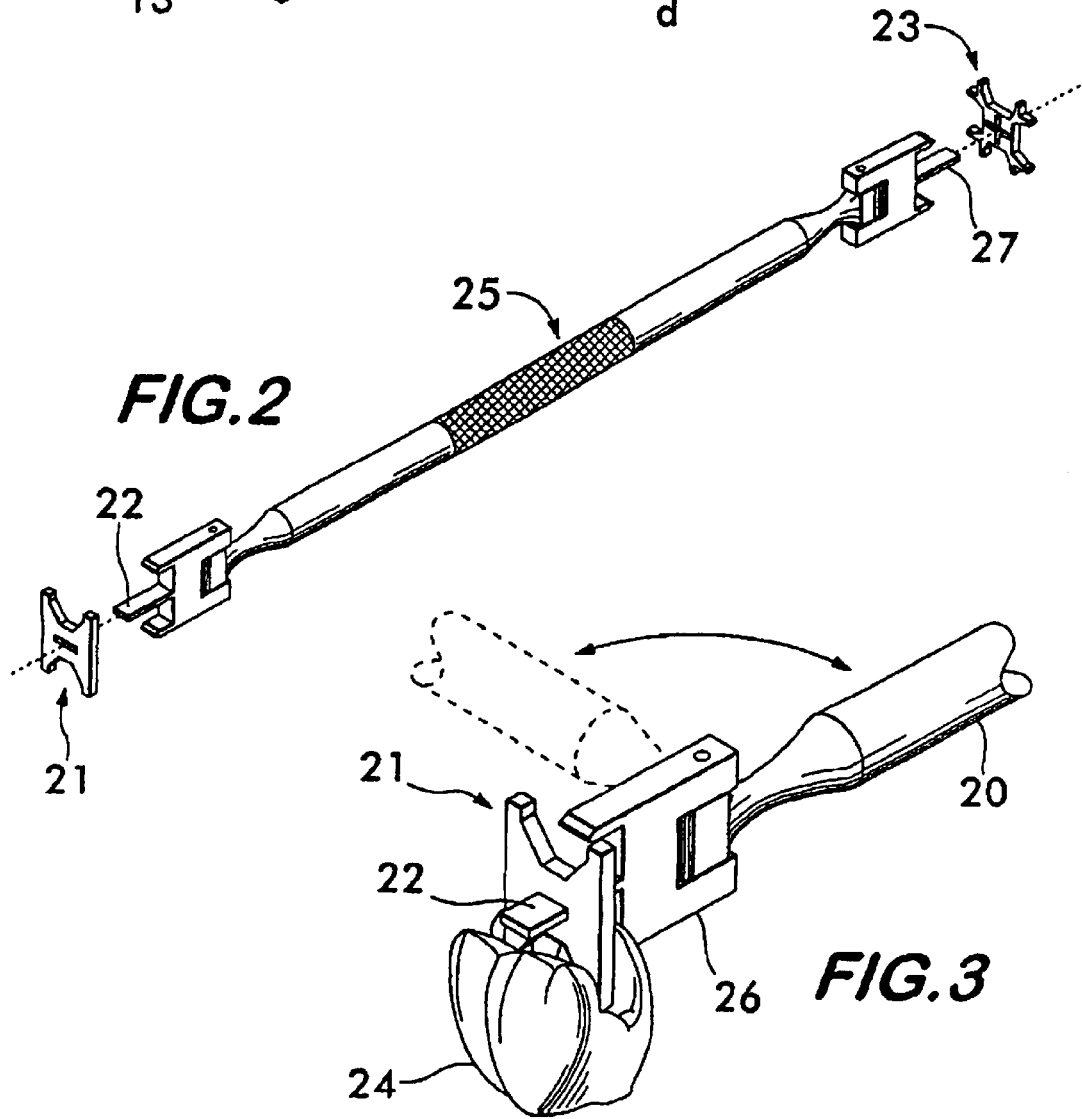

US 6,783,359 B2

ORTHODONTIC MARGINAL RIDGE MEASUREMENT DEVICE

FIELD OF THE INVENTION

The present invention relates to an orthodontic procedure to properly place brackets on human teeth. More specifically, it relates to a device for placement of the bracket with respect to the marginal ridges of the teeth.

BACKGROUND OF THE INVENTION

The present invention relates to my previous invention described in U.S. Pat. No. 6,296,482 entitled "Orthodontic Height Positioning Gauge with Rotatable Heads" issued on Oct. 2, 2001. That patent describes a method for placement of orthodontic brackets on human teeth by locating them using a hand-held measurement device. That document is hereby incorporated by reference as though fully set forth. This previous invention describes a height gauge by which brackets are located on individual teeth by measuring the distance from the cusp tip of each tooth.

However, there is a problem with gauges of this type. Although the cusp tip is used as the point of reference for measurement, it is the marginal ridges of the teeth which are the true desired points of alignment for the brackets. This can create inaccuracies because ridge-to-cusp distances vary. Past height gauges may have the facility for compensating for different ridge-to-cusp tip distances, however this requires an additional degree of judgment on the part of the clinician which can introduce the possibility of yet greater error. Furthermore, these height gauges rest on the cusp tip and thus have only one point of contact. Therefore, they can easily be incorrectly angled so that the measurement taken is not accurate.

Given the state of the art in tooth measurement for proper orthodontic bracket placement, there is therefore a need for a device which directly determines the correct bracket placement on the facial surface of a human tooth using the tooth's marginal ridges as the direct reference point for measurement. Furthermore, there is a need in the art for a device which directly measures bracket-to-marginal ridges directly that is conveniently hand-held and easy to use.

SUMMARY OF THE INVENTION

In order to meet the needs in the art, the present marginal ridge measurement plate has been devised as an attachment to my previous height gauge as described in my aforementioned U.S. Pat. No. 6,296,482. This attachment slides onto the center tab of the height gauge. In use, vertically-extending legs of the marginal ridge measurement plate rest on mesial and distal marginal ridges of the tooth. The plate is shaped so that while the legs rest directly on the marginal ridges, a cut-out portion between the legs avoids contact and interference from the inward-facing slopes of the tooth cusps. The attachment plate is slidably fitted to the head of the height gauge by a slot which is fitted to the center tab or member so that after the bracket is placed on the tooth, the gauge can be moved directly out from the archwire slot without disturbing the bracket position. The slot is centered on a line between the legs and, since the vertically-extending legs of the marginal ridge attachment plate each rests on the mesial and distal marginal ridges, the attachment plate also centers the bracket in the middle of the facial surface of the tooth. Furthermore, the gauge also holds the bracket placement post parallel to the marginal ridges. Thus, the measurement plate not only establishes the correct bracket height but also centers and properly aligns the horizontal angulation of the bracket on the tooth.

More specifically, the applicant has invented a planar measurement plate for attachment to an orthodontic height gauge having a cusp contact tab and a bracket locating post comprising a body portion that includes a rectangular slot adapted to closely and slidably receive the cusp tab. A first pair of vertically-extending legs of substantial length on the attachment include a cut-out region between the legs to avoid contact from inward-sloping sides of the cusp of the tooth when distal ends of the legs are placed against the mesial and distal ridges of the tooth. The attachment may further include a second pair of vertically-extending legs on a second side of the plate opposite the first pair of legs. Furthermore, the attachment may include a total of four pairs of outwardly extending legs each separated 90 degrees and extending from each of four sides of the attachment plate. With each pair of legs separated a different distance apart, that the same attachment may be used to measure the distances of four different sizes of teeth by locating the attachment plate on the height gauge center tab in any one of four different slidable positions. The capability of the attachment plate to achieve four different positions is facilitated by a pair of centrally located slots oriented at 90 degrees from each other. It should be understood that several attachment plates may be provided all having multiple pairs of legs separated by different distances.

Other objects and advantages of the invention will be readily apparent to those of skill in the art from the following drawings and description of the preferred embodiment. For example, the present invention can be used with an implement with non-rotatable heads for placing brackets on models in the laboratory for indirect bonding.

BRIEF DESCRIPTION OF THE DRAWINGS

FIG. 1 is a top right front isometric view of the attachment of the present invention.

FIG. 1A is a top right front isometric view of an alternate embodiment of the invention.

FIG. 2 is a top right front isometric view of the embodiments shown in FIGS. 1 and 1A in assembly position with an orthodontic height gauge.

FIG. 3 is a top right front isometric view of the height gauge and attachment of the invention shown in use on a tooth with an alternate position rotatable handle shown in phantom.

DESCRIPTION OF THE PREFERRED EMBODIMENT

Figure 4:
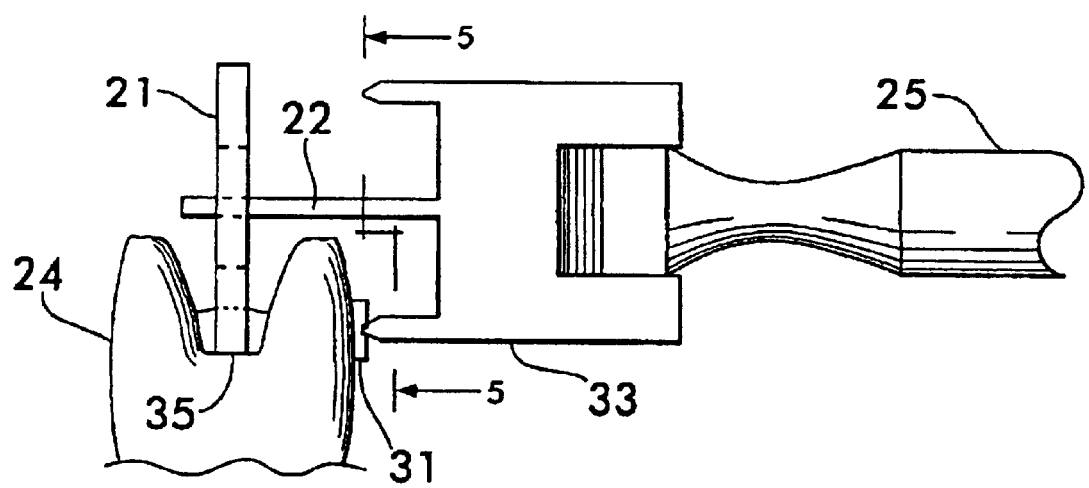
FIG. 4 is a side view of the elements of the invention shown in FIG. 3.

Referring now to FIG. 1, a basic form of the attachment plate which embodies the invention is shown. This embodiment shows two pairs of vertically-extending legs, one pair 11 facing upward and the second pair 13 facing downward. Each pair is separated a different distance to accommodate teeth of two different widths. A center slot 17 is provided through the planar main body 15 which slidably receives a height gauge cusp tab or center member as shown in FIGS. 2 through 5. By inverting the plate 180 degrees the pairs of legs are reversed in position and the opposite pair may then be used. FIG. 1A shows an alternate embodiment with four pairs of legs and two slots 19 oriented 90 degrees to each other. This embodiment permits the attachment plate to be placed in four different positions on the height gauge center tab to utilize the four different possible spacings a, b, c, and d of the legs.

Referring now to FIG. 2, a height gauge 25 is shown in which both of the attachment plate embodiments 21 and 23 of FIGS. 1 and 1A are shown in assembly position. The attachments are placed over either of the height gauge cusp tabs 22 or 27 so that the tab fits through a slot in the center of the body portion of the attachment plate. This permits the plate to be easily fitted to the working end of the height gauge and also provides a slidable attachment which is important to its operation.

FIG. 3 shows the attachment plate 21 in use on a tooth 24. As shown in this figure, the pair of downward-extending legs rest on the mesial and distal marginal ridges of the tooth. It will be readily appreciated that this holds the tab 22, and hence the rotatable head 26 of the gauge, a selected height with respect to the tooth. Shown in this figure is an alternate position of handle 20 depicted in dotted lines which illustrates the operation of the rotatable head 26 of the height gauge.

Referring now to FIG. 4, a side view of the elements shown in FIG. 3 is depicted with a bracket to be placed. An orthodontic bracket 31 is positioned by the lower gauge post 33 against the facial surface of the tooth 24 at a distance measured directly from the marginal ridges 35 of the tooth by plate 21 fitted over tab 22. Once the bracket 31 has been properly positioned, the height gauge 25 may be withdrawn directly away from the tooth allowing the bracket alignment post to be withdrawn from the bracket archwire slot without disturbing its positioning.

Figure 5:
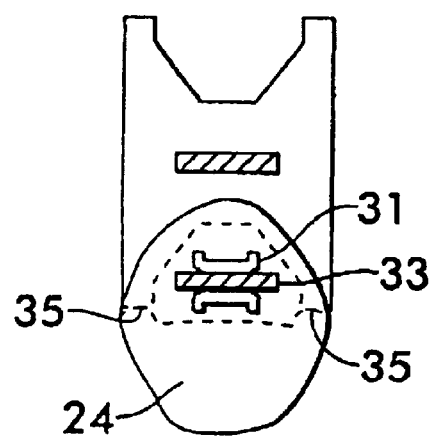
FIG. 5 is a rear sectional view taken from FIG. 4 as shown in that figure.
Figure 6:
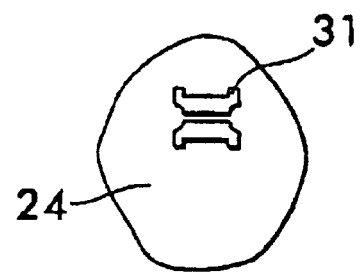
FIG. 6 is a front view of a tooth showing proper placement of an orthodontic bracket on the facial surface thereof utilizing the invention.

FIG. 5 shows the positioning of elements shown in FIG. 4 and also demonstrates that not only is the height positioning of the bracket 31 on the tooth 24 directly measured from the marginal ridges 35, but also when the bracket is centered on the height gauge arm 33, the bracket becomes centered on the facial surface of the tooth and is parallel to the marginal ridges with correct horizontal angulation. FIG. 6 shows the resulting proper placement of the orthodontic bracket 31 on the facia of the tooth 24 after use of the invention as shown in FIGS. 3 through 5 as described above.

It should be understood that there may be other modifications and changes to the present invention that will be obvious to those of skill in the art from the foregoing description, however the present invention should be limited only by the following claims and their legal equivalents.

What is claimed is:

1. An attachment for an orthodontic height gauge having a cusp tab and a bracket locating post, comprising:
    a planar body portion including a rectangular slot, said slot adapted to closely and slidably receive said height gauge cusp tab;
    a first pair of spaced apart vertically-extended legs of substantially equal length separated by a first distance;
    a second pair of spaced apart vertically-extended legs of substantially equal length separated by a second distance, said second pair of legs lying on the opposite side of said rectangular slot from said first pair of legs; and
    a cut-out region between said legs for avoiding contact with the inward-sloping sides of a cusp of a tooth when distal ends of said legs are placed against the mesial and distal ridges of said tooth.

2. An orthodontic bracket placement gauge, comprising:
    a bracket height gauge having a cusp contact tab and a bracket locating arm insertable into an archwire slot of said bracket;
    an attachment plate comprising a body, a first pair of vertically-extending legs spaced apart a first distance, each leg for contacting a marginal ridge of a human tooth, and a cut-out located between said legs for receiving the inward-sloping sides of a cusp of said tooth when distal ends of said legs are placed against the marginal ridges; and
    said attachment plate further including a rectangular slot, said slot adapted to closely and slidably receive said height gauge cusp contact tab.

3. The bracket placement gauge of claim 2 wherein said legs extend from a first side of said plate opposite a second side of said plate which includes a second pair of vertically-extending legs spaced apart a second distance.

4. The orthodontic placement gauge of claim 3 further including a third side of said attachment plate including a third pair of legs oriented at 90 degrees to said first and second pairs of legs and further including a second rectangular slot coaxial with said first rectangular slot oriented radially 90 degrees thereto, said third pair of legs spaced a third distance apart.

5. The orthodontic bracket placement gauge of claim 4 further including a fourth side of said attachment plate which includes a fourth pair of legs opposite said third pair of legs extending outwardly from said body portion, said fourth pair of legs being spaced apart a fourth distance.

6. A hand-held dental instrument comprising:
    an elongate handle having a rotatable head at a first end;
    a center tab longitudinally extending from the center of said head;
    an orthodontic bracket positioning arm extending longitudinally from said head, said arm being parallel to said tab and spaced a gauge distance from a first side of said tab; and
    a measurement plate including a rectangular slot, said slot adapted to closely and slidably receive said tab.

7. The dental instrument of claim 6 wherein said measurement plate includes two vertically-extended legs of substantially equal length and a cut-out region between said legs for receiving the inward-sloping sides of a cusp of a tooth when the distal ends of said legs are placed against the mesial and distal ridges of said tooth.

8. The dental instrument of claim 7 further including a second orthodontic bracket positioning arm longitudinally extending from said head, said arm spaced a second gauge distance from an opposite side of said center tab.

9. The dental instrument of claim 7 wherein the second gauge distance is different from said first gauge distance.

10. The dental instrument of claim 7 wherein said head includes a yoke and hinge means for rotatably affixing said head to said handle.

11. The dental instrument of claim 7 wherein said yoke includes detent means for releasably holding said head at an angle with respect to said handle.

12. The dental instrument of claim 7 wherein the detent means includes a spring-biased plunger located between opposing arms of said yoke, whereby said plunger forceably contacts positioning means on the end of said handle.

13. The dental instrument of claim 7 further including a second rotatable head located on an opposite end of said handle from said first rotatable head, said second head being of substantially identical construction as said first head except that the gauge distances of the second head includes third and fourth gauge distances which are different than said first and second gauge distances.

* * * * *